United States Patent [19]

McCarthy

[11] Patent Number: 5,396,003
[45] Date of Patent: Mar. 7, 1995

[54] RECOVERY AND PURIFICATION OF 1,1,2-TRICHLOROETHANE FOR REUSE IN THE PRODUCTION OF IOVERSOL

[75] Inventor: William Z. McCarthy, St. Louis, Mo.

[73] Assignee: Mallinckrodt Medical PMC, Las Vegas, Nev.

[21] Appl. No.: 68,496

[22] Filed: May 27, 1993

[51] Int. Cl.$^6$ .................... C07C 17/38; C07C 19/05; C07C 233/00
[52] U.S. Cl. .................................. 570/262; 564/153; 564/156; 424/5; 570/263
[58] Field of Search ............... 564/153, 156; 570/213, 570/262, 190, 191, 263; 424/5

[56] References Cited

U.S. PATENT DOCUMENTS

| 3,148,041 | 9/1964 | Dehn et al. | 570/262 |
| 3,197,941 | 8/1965 | Colton et al. | 570/262 |
| 4,997,983 | 3/1991 | McCarthy | 564/153 |

FOREIGN PATENT DOCUMENTS

| 292333 | 7/1991 | Germany | 570/262 |
| 55500 | 5/1968 | Poland | 570/262 |

*Primary Examiner*—Shailendra Kumar
*Attorney, Agent, or Firm*—Rita Downard Vacca

[57] ABSTRACT

A process for the recovery and purification of 1,1,2-trichloroethane from the intermediates produced for the production of ioversol for reuse thereof.

3 Claims, No Drawings

RECOVERY AND PURIFICATION OF 1,1,2-TRICHLOROETHANE FOR REUSE IN THE PRODUCTION OF IOVERSOL

FIELD OF THE INVENTION

This invention relates to a process for the recovery and purification of 1,1,2-trichloroethane hereinafter called "TCE". More particularly, this invention relates to the recovery and purification of 1,1,2-trichloroethane from the preparation of 5-amino-N,N'-bis(2,3-diacetoxypropyl)-2,4,6-triiodoisophthalamide, 5-acetoxyacetamido-N,N'-bis(2,3-diacetoxypropyl)-2,4,6-triiodoisophthalamide and 5-[N-(2-acetoxyethyl)acetoxyacetamido]N,N'-bis(2,3-diacetoxypropyl)-2,4,6-triiodoisophthalamide, intermediates in the production of Ioversol.

BACKGROUND OF THE INVENTION

Ioversol was disclosed as a useful nonionic x-ray contrast agent in U.S. Pat. No. 4,396,598. One intermediate used in the production of ioversol is 5-amino-N,N'-bis(2,3-diacetoxypropyl)-2,4,6-triiodoisophthalamide having the following structure:

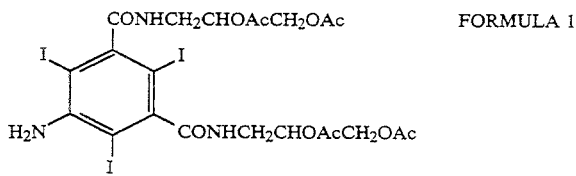

FORMULA 1

Another intermediate used in the production of ioversol is 5-acetoxyacetamido-N,N'-bis(2,3-diacetoxypropyl)-2,4,6-triiodoisophthalamide having the following structure:

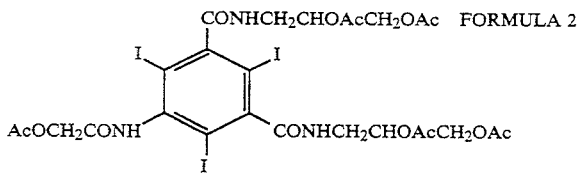

FORMULA 2

Still another intermediate used in the production of ioversol is 5-[N-(2-acetoxyethyl)acetoxyacetamido]N,N'-bis(2,3-diacetoxypropyl)-2,4,6-triiodoisophthalamide having the structure:

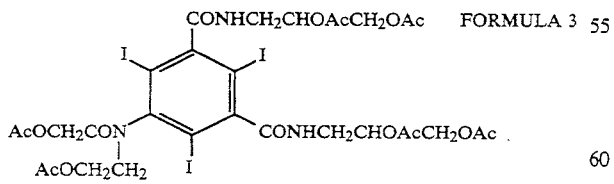

FORMULA 3

These intermediate compounds and their use in the production of ioversol are disclosed in detail in U.S. Pat. No. 4,396,598 incorporated herein by reference.

These intermediates are used in various synthetic steps to produce ioversol, a compound of the following structure:

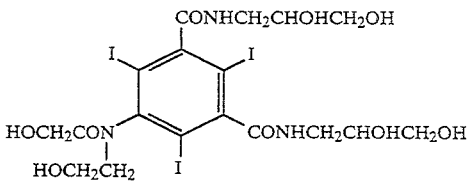

FIGURE 4

The procedure used to produce ioversol heretofore used large quantities of 1,1,2-trichloroethane (TCE) as a reaction and extraction solvent for several processes in the preparation of the above-described intermediates. Due to the large quantities of TCE required in the production of ioversol and the high cost thereof, an alternative method of producing ioversol which allows for the recovery and high quality purification of TCE from the ioversol production process is desired. It is an object of the present invention to meet this need.

SUMMARY OF THE INVENTION 1,1,2-Trichloroethane (TCE) is used as a reaction and extraction solvent for several processes in the preparation of several ioversol intermediates as noted above. TCE is removed from these intermediates by evaporation and condensation. TCE is also recovered from waste water streams and an amylacetate mother liquor stream in the same manner. This recovered TCE can be recycled for reuse. However, the final quality of the recovered TCE is quite low, due to impurities, compared to using virgin TCE. Therefore, the reuse of recovered TCE is not ideal.

The purification process of the present invention was thus developed to recover and purify TCE to a high quality for reuse. The TCE recovered by evaporation and condensation for purification according to the present invention is contaminated with a wide variety of impurities such as dimethylsulfoxide (DMSO) and other sulfides as well as other process reagents. The purification process of the present invention requires three steps, namely a reactive extraction, a drying distillation and a separation distillation, each to be discussed in detail below.

The recovery and purification process of the present invention has the advantage of allowing for the reuse of purified high quality TCE, an expensive solvent used in the production of ioversol. The present invention is thereby commercially useful, economical and environmentally progressive.

DETAILED DESCRIPTION OF THE INVENTION 1,1,2-Trichloroethane (TCE) is used as a reaction and extraction solvent for several processes in the preparation of Ioversol intermediates. The TCE solvent is removed from the ioversol intermediates described above by evaporation and condensation. The solvent, TCE, is also recovered from waste water streams and an amylacetate mother liquor stream by evaporation and condensation, i.e., distillation. TCE recovered in this manner is unsuitable for the preparation of high quality intermediates as desired in commercial drug processing. A unique purification process has thus been developed to recover and purify the TCE solvent in a quality suitable for reuse. The solvent when recovered is contaminated with a wide variety of impurities such as DMSO and other sulfides as well as other process reagents which makes the purification of TCE difficult.

Due to the difficulty of removing sulfides from the recovered TCE solvent, the purification achieved by the present invention is unexpected.

The subject purification process for 1,1,2-trichloroethane requires three steps. The first step in the purification process is a reactive extraction which may be carried out with any suitable aqueous, acidic oxidizing reagent, such as chlorine dissolved in water, manganese oxide, or oxides of nitrogen. Chlorine water, is the preferred oxidizing reagent for this extraction solution because it is an acidic oxidizing reagent. Basic aqueous oxidants such as sodium hypochlorite are not suitable for use with TCE. Basic aqueous oxidizing reagents cause a sequence of reactions to take place in the presence of TCE whereby HCl is eliminated or extracted from the TCE to form vinylidine chloride. If the oxidizing reagent is highly basic, the reaction continues and another HCl is eliminated from the vinylidine chloride to form chloroacetylenes which are potentially explosive and thereby hazardous! Oxygen and hydrogen peroxide should likewise be avoided as an oxidizing reagent for this reaction due to incompatibility with impurities which potentially could be explosive. The acidic oxidation of TCE is necessary to reduce the level of sulfide impurities. Distillation, alone, is not effective in removing sulfides from 1,1,2-trichloroethane because the boiling points are not sufficiently different. Instead, the sulfides are oxidized with chlorine to form sulfur chlorides which hydrolyze in the presence of water to form sulfur oxides. Sulfur oxides are soluble in water and may be removed by extraction and/or distillation. Some sulfur compounds such as dimethylsulfoxide (DMSO) are oxidized further to sulfones which are also water soluble. In addition to increasing the water solubility of the sulfur species, these newly oxidized compounds have boiling points which are higher than the resulting water-saturated 1,1,2-trichloroethane, which has a boiling point of 110°–115° C. as compared to DMSO which has a boiling point of 189° C. This difference in boiling points simplifies the purification of TCE considerably.

The second step for the present purification process is a drying distillation which removes water, excess chlorine and other low boiling point impurities from the water-saturated TCE. A second principal low boiling point impurity which is removed by this process is vinylidine chloride. The distillation of the water-saturated 1,1,2-trichloroethane forms an azeotrope in this step which dries the TCE. The overheads from this distillation are condensed and form two layers. Some of the organic layer which contains 1,1,2-trichloroethane and vinylidine chloride may be returned to the distillation column to increase yield.

The third step of the present invention is a distillation step to separate high boiling point materials, such as dimethylsulfoxide, dimethylsulfone, methane sulfonic acid and dimethylacetamide, from 1,1,2-trichloroethane. Residual high boiling impurities such as the sulfoxides and traces of other organic compounds from the manufacturing process such as dimethylacetamide can be removed by this distillation process. However, the distillation could require a multiplate distilling column depending on the purity requirements necessary for reuse.

The Purification process of the present invention is described in still greater detail, and may be carried out according to the following specific example:

EXAMPLE 1

A pilot plant scale test was run to demonstrate the chlorine oxidation, drying, and purification of 1,1,2-trichloroethane. A sample of TCE recovered from the ioversol factory was spiked with sulfur compounds to give approximately 100 ppm by weight of dimethylsulfide and 200 ppm by weight each of dimethyldisulfide and dimethylsulfoxide.

The spiked TCE was mixed with chlorine saturated water in a continuous flow stirred tank reactor. The flow rates had a ratio of about 100 mL/min TCE, 1 gram/min chlorine and 14 mL/min water. The reactor mixture was admitted to a separator which separated the chlorine saturated TCE and from the aqueous phase. A water recycle loop was used to return water to the reactor at 40 mL/min. The TCE was then fed to a drying distillation column which separated light boiling compounds e.g. water, vinylidine chloride and chlorine, from TCE. The TCE product from this column contained less than 100 ppm water and less than 1 ppm of organic sulfur compounds. Dry TCE was then vacuum distilled at ca. 200 mm Hg. The product was highly purified TCE.

As various changes could be made in the above process without departing from the scope of the present invention, it is intended that all matter contained in the above description or shown in the above formulas shall be interpreted as illustrative and not in a limiting sense.

What is claimed is:

1. A process for the recovery and purification of 1,1,2-trichloroethane from a process stream for the production of ioversol comprising the steps of:
   a) removing 1,1,2-trichloroethane from ioversol intermediates by distillation;
   b) extracting said 1,1,2-trichloroethane with an aqueous oxidizing reagent selected from the group consisting of chlorine dissolved in water, manganese oxides, oxygen and oxides of nitrogen to form water-saturated 1,1,2-trichloroethane;
   c) distilling said water-saturated 1,1,2-trichloroethane which forms an azeotrope for drying thereof to produce 1,1,2-trichloroethane; and
   d) distilling said 1,1,2-trichloroethane to remove high boiling point impurities.

2. The process of claim 1 wherein said ioversol intermediates include 5-amino-N,N'-bis(2,3-diacetoxypropyl)-2,4,6-triiodoisophthalamide, 5-acetoxyacetamido-N,N'-bis(2,3-diacetoxypropyl)-2,4,6-triiodoisophthalamide and 5-[N-(2acetoxyethyl)acetoxyacetamido]N,N'-bis(2,3-diacetoxyethyl)-2,4,6-triiodoisopthalamide.

3. The process of claim 1 wherein said high boiling point impurities include dimethylsulfoxide, dimethylsulfone, methane sulfonic acid and dimethylacetamide.

* * * * *